(12) United States Patent
Ren et al.

(10) Patent No.: US 9,675,244 B1
(45) Date of Patent: Jun. 13, 2017

(54) LOCATION INDICATOR FOR OPTICAL COHERENCE TOMOGRAPHY IN OPHTHALMIC VISUALIZATION

(71) Applicant: Novartis AG, Basel (CH)

(72) Inventors: Hugang Ren, Fort Worth, TX (US); Lingfeng Yu, Fort Worth, TX (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/957,306

(22) Filed: Dec. 2, 2015

(51) Int. Cl.
| | |
|---|---|
| A61B 3/14 | (2006.01) |
| A61B 3/00 | (2006.01) |
| A61B 3/10 | (2006.01) |
| A61B 3/13 | (2006.01) |
| A61B 34/20 | (2016.01) |

(52) U.S. Cl.
CPC ............ *A61B 3/102* (2013.01); *A61B 3/0025* (2013.01); *A61B 3/0058* (2013.01); *A61B 3/13* (2013.01); *A61B 3/14* (2013.01); *A61B 34/20* (2016.02); *A61B 2034/2055* (2016.02)

(58) Field of Classification Search
USPC ................................................. 351/200–246
See application file for complete search history.

(56) References Cited

U.S. PATENT DOCUMENTS

| | | | |
|---|---|---|---|
| 2013/0148080 A1 | 6/2013 | Sander | |
| 2013/0194544 A1 | 8/2013 | Iwase et al. | |
| 2013/0271757 A1* | 10/2013 | Kang | A61B 3/102 356/300 |
| 2014/0024949 A1 | 1/2014 | Wei et al. | |
| 2014/0285811 A1 | 9/2014 | Brennan et al. | |
| 2015/0359426 A1* | 12/2015 | Buckland | A61B 3/102 600/425 |

FOREIGN PATENT DOCUMENTS

| | | |
|---|---|---|
| DE | 102013210728 A1 | 12/2014 |
| WO | 2016/151491 A1 | 9/2016 |
| WO | 2016/185363 A1 | 11/2016 |

* cited by examiner

*Primary Examiner* — Mohammed Hasan
(74) *Attorney, Agent, or Firm* — S. Brannon Latimer

(57) ABSTRACT

An ophthalmic visualization system can include a computing device in communication with an OCT system configured to scan a surgical field to generate an OCT image. The computing device can be configured to determine locations within the surgical field corresponding to locations within the OCT image. The ophthalmic visualization system can also include an indicator mechanism in communication with the computing device and a surgical microscope configured to image the surgical field. The indicator mechanism can be configured to cause a location indicator to be positioned within a field of view of the surgical microscope. The location indicator can graphically represent the locations within the surgical field corresponding to the locations within the OCT image.

18 Claims, 10 Drawing Sheets

LOCATION INDICATOR FOR OPTICAL COHERENCE TOMOGRAPHY IN OPHTHALMIC VISUALIZATION

BACKGROUND

Technical Field

Embodiments disclosed herein can be related to ophthalmic visualization systems. More specifically, embodiments described herein can relate to providing a location indicator in a field of view of surgical microscope during an ophthalmic surgical procedure. The location indicator can allow a surgeon to correlate locations within an optical coherence tomography (OCT) image with locations in the surgical field, such as a patient's eye.

Related Art

Ophthalmic microsurgical procedures can require precision cutting and/or removing of various body tissues of the patient's eye. A user, such as a surgeon or other medical professional, can visualize the patient's eye using a surgical microscope. Image-guided surgical intervention can be possible with technologies such as optical coherence tomography (OCT). OCT can be a noninvasive, high resolution, cross-sectional imaging modality. The OCT image can guide the surgeon during the ophthalmic surgical procedure. However, the surgeon can find it difficult to identify where in the patient's eye anatomical features shown in the OCT image are located.

Accordingly, there remains a need for improved devices, systems, and methods that allow the surgeon to correlate locations within the patient's eye and the OCT image by addressing one or more of the needs discussed above.

SUMMARY

The presented solution fills an unmet medical need with a unique solution to quickly and accurately determine the physical location of an anatomical feature shown in an OCT image. An ophthalmic visualization system described herein provides a location indicator in the field of view of a surgical microscope. For example, a display device and/or a beam source can output the location indicator so as to be viewable by the surgeon with the surgical microscope. The location indicator can include information about multiple locations within an OCT image. For example, graphics along a length of the location indicator can vary so as to graphically represent corresponding locations within the surgical field and the OCT image. Using the location indicator, the surgeon can quickly and accurately determine the physical location of the anatomical feature within the surgical field based on the OCT image.

Consistent with some embodiments, an ophthalmic visualization system can be provided. The ophthalmic visualization system can include a computing device in communication with an OCT system configured to scan a surgical field to generate an OCT image. The computing device can be configured to determine locations within the surgical field corresponding to locations within the OCT image. The ophthalmic visualization system can also include an indicator mechanism in communication with the computing device and a surgical microscope configured to image the surgical field. The indicator mechanism can be configured to cause a location indicator to be positioned within a field of view of the surgical microscope. The location indicator can graphically represent the locations within the surgical field corresponding to the locations within the OCT image.

Consistent with some embodiments, a method of visualizing an ophthalmic surgical procedure. The method can include scanning a surgical field using an OCT system. The method can also include determining, using a computing device in communication with the OCT system, locations within the surgical field corresponding to locations within an OCT image. The OCT image can be generated based on the scanning the surgical field using the OCT system. The method can also include outputting a location indicator within a field of view of a surgical microscope viewing the surgical field. The location indicator can graphically represent the locations within the surgical field corresponding to the locations within the OCT image.

Additional aspects, features, and advantages of the present disclosure will become apparent from the following detailed description.

Figure 1:
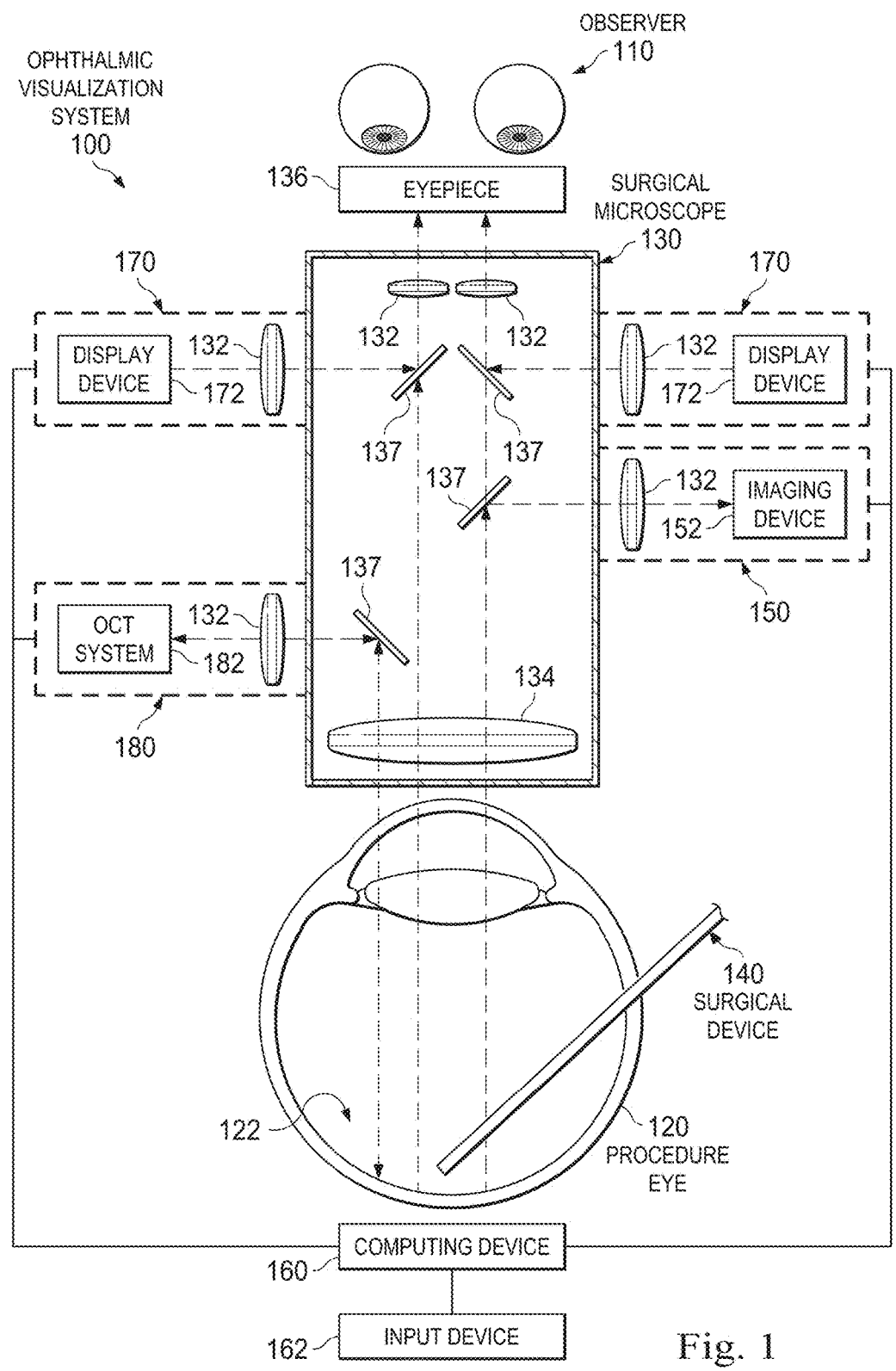
FIG. 1 is a schematic diagram illustrating an ophthalmic visualization system.

In the drawings, elements having the same designation have the same or similar functions.

DETAILED DESCRIPTION

In the following description, specific details can be set forth describing certain embodiments. It will be apparent, however, to one skilled in the art that the disclosed embodiments may be practiced without some or all of these specific details. Specific and/or illustrative, but not limiting, embodiments can be presented herein. One skilled in the art will realize that other material, although not specifically described herein, can be within the scope and spirit of this disclosure.

The present disclosure describes devices, systems, and methods of encoding point-to-point location correspondence between the OCT image and the surgical field into a location indicator. The location indicator can be positioned in the field of view of the surgical microscope used by the surgeon to visualize the surgical field. The OCT image and a key corresponding to the location indicator can also be viewable within the field of view of the surgical microscope. The location indicator and the key can be visually similar in that they include different graphics, such as text, numerals, shapes, symbols, colors, patterns, images, scale bars, a color gradient, a ruler, and/or beam spots of varying wavelength, varying spot size, and/or varying brightness, that vary along a length of a B-scan of an OCT system. By identifying a location in the OCT image and the graphic in the key aligned with that location, the corresponding physical location in the surgical field can be determined by locating the corresponding graphic in the location indicator. The location indicator can be a light beam transmitted onto the surgical field by a beam source or a graphical overlay output into the field of view of the surgical microscope.

The devices, systems, and methods of the present disclosure provide numerous advantages, including:

(1) Integration of OCT imaging in ophthalmic surgical procedures for image-guided surgical interventions can be improved. While some OCT systems can be implemented to guide ophthalmic surgical interventions, utilizing the OCT image can be challenging. In this context, the location indicator allowing the surgeon to quickly and accurately determine corresponding locations within the OCT image and the surgical field can facilitate meaningful OCT-guided surgical interventions.

(2) The surgeon can more accurately identify corresponding physical locations of anatomical features pictured in the OCT image. While some OCT systems utilize a monochromatic aiming beam to assist the surgeon in determining the location of the OCT image, the aiming beam identifies only the B-scan location. The surgeon must perform complex and sometimes inaccurate spatial interpretation in his or head during the procedure to identify the location of anatomy of interest within the surgical field. In this context, the location indicator with varying image characteristics across its length can allow the surgeon to more accurately identify A-line scan locations associated with the anatomy of interest.

(3) The surgeon can utilize OCT image guidance more quickly and conveniently. With the location indicator having varying image characteristics across its length, the surgeon can quickly determine the corresponding physical location of anatomy of interest illustrated in the OCT image. The surgeon can advantageously avoid tedious and time-consuming spatial interpretation work during ophthalmic surgical procedure to identify the corresponding physical location.

(4) The surgical workflow can be improved by allowing the surgeon to replace slow and inaccurate steps of manually identifying the physical location of anatomy of interest shown in the OCT image with faster and more accurate steps of utilizing the location indicator to determine the corresponding physical location.

(5) The safety of the patient can be improved by facilitating increased situational awareness for the surgeon. The location indicator with varying image characteristics across its length can allow the surgeon to efficiently and accurately establish point-to-point correspondence between the surgical field and the OCT image.

Figure 2:
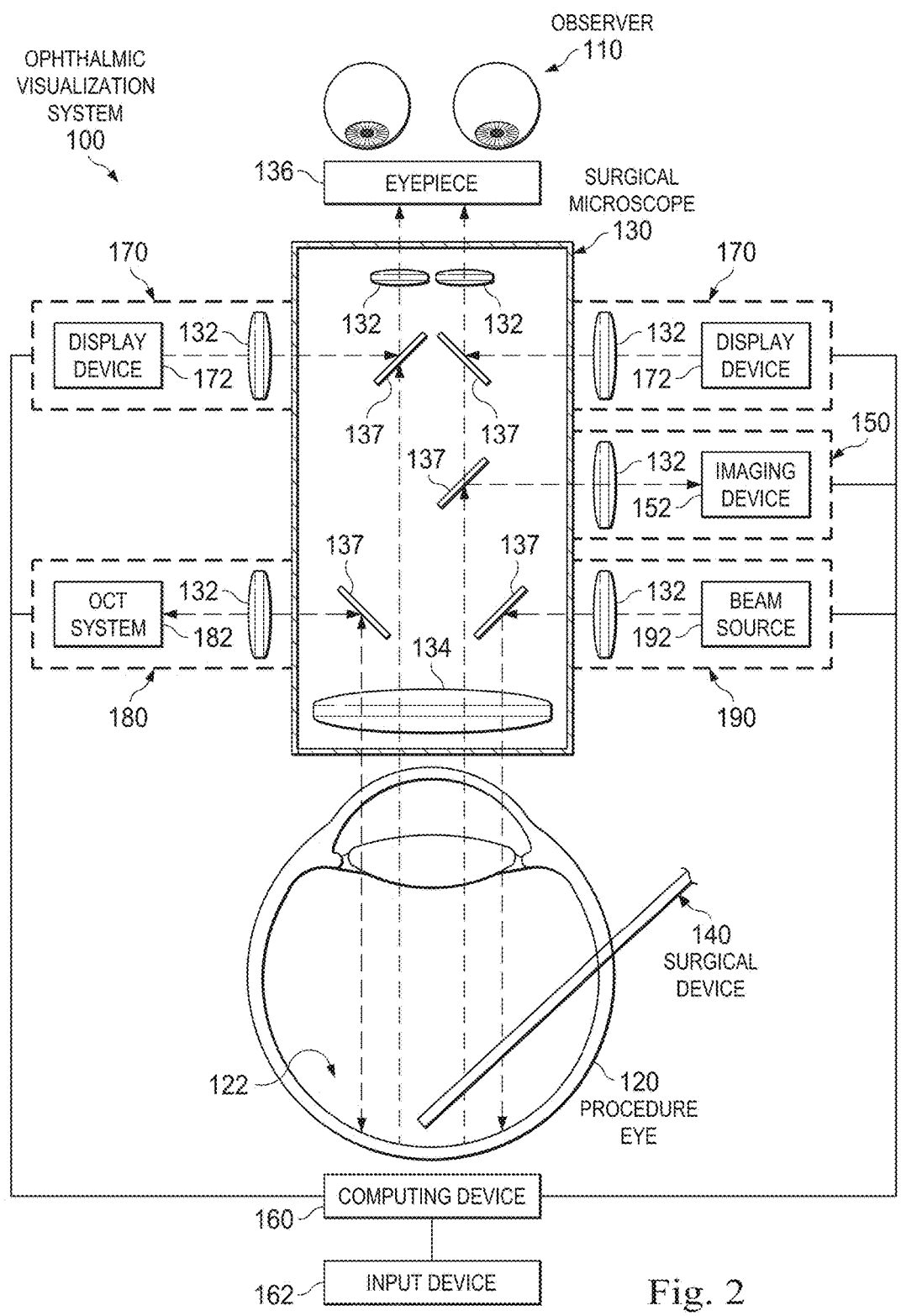
FIG. 2 is a schematic diagram illustrating an ophthalmic visualization system.

FIGS. 1 and 2 illustrate an ophthalmic visualization system 100. The ophthalmic visualization system 100 can include a computing device 160 in communication with an OCT system 182. The OCT system 182 can be configured to scan a surgical field 122 to generate an OCT image. Exemplary OCT images can be illustrated in FIGS. 3-8. The computing device 160 can be configured to determine locations within the surgical field 122 corresponding to locations within the OCT image. The ophthalmic visualization system 100 can include an indicator mechanism, such as a display device 172 and/or a beam source 192. The indicator mechanism can be in communication with the computing device 160 and a surgical microscope 130 configured to image the surgical field 122. The indicator mechanism can be configured to cause a location indicator to be positioned within a field of view of the surgical microscope 130. Exemplary location indicators can be illustrated at least in FIGS. 4 and 6-9D. The location indicator can graphically represent the locations within the surgical field 122 corresponding to the locations within the OCT image.

The observer 110, such as a surgeon or other medical professional, can visualize the surgical field 122 using the surgical microscope 130. During the surgical procedure, a surgical device 140 can be inserted into the procedure eye 120. In a vitrectomy procedure, for example, the surgical device 140 can be inserted into the vitreous chamber via an incision through the sclera in the pars plana. The surgical device 140 can be a cutting probe, a vitrectomy probe, laser probe, an ablation probe, a vacuum probe, a flushing probe, scissors, forceps, other suitable ophthalmic devices, and/or combinations thereof. Various other ophthalmic tools, such as a light source, an infusion cannula, etc., can also be inserted into the procedure eye 120 during the surgical procedure. The observer 110 can carry out the surgical procedure in the surgical field 122 using the surgical device 140. The surgical field 122 can include various biological tissue in the procedure eye 120, including the vitreous humor, transparent membranes, blood vessels, retina, macula, foveola, fovea centraalis, para fovea, perifovea, optic disc, optic cup, and/or other portions of the procedure eye 120. The surgical field 122 can also include one or more layers of the retina, including the inner limiting membrane, nerve fiber layer, ganglion cell layer, inner plexiform layer, inner nuclear layer, outer plexiform layer, outer nuclear layer, external limiting membrane, layer of rods and cones, and/or retinal pigment epithelium.

The surgical microscope 130 can be configured to image the surgical field 122. The surgical microscope 130 can be any suitable surgical microscope configured for use during an ophthalmic procedure. The surgical microscope can be an optical microscope and/or a digital microscope. In that regard, the surgical microscope 130 can include one or more lenses 132, such as focusing lens(es), zoom lens(es), and an objective lens 134, as well as mirrors, filters, gratings, and/or other optical components that comprise an optical train. Light reflected from the surgical field 122 can be received by the surgical microscope 130 and visualized by the observer 110, who views an enface, fundus image of the surgical field 122 through an eyepiece 136. Exemplary views of the surgical field 122 using the ophthalmic visualization system 100 and the surgical microscope 130 can be shown in FIGS. 3-8. With a stereo microscope, two optical paths (e.g., one for each eye of the observer 110) can be provided. Similarly, the eyepiece 136 can include separate oculars or other viewing components for each eye of the observer 110. As described herein, the observer 110 can also view the location indicator identifying corresponding locations of an OCT image and the surgical field 122 with the surgical microscope 130.

The OCT system 182 can be a microscope-integrated or standalone component of the ophthalmic visualization system 110. The OCT system 182 can be configured to scan the surgical field 122. The diagnostic utility of the OCT system 182 can result from its non-contact high resolution and depth-resolved imaging capability. The computing device 160 can generate an OCT image based on data obtained by the OCT system 182. As described herein, the cross-sectional OCT image can be provided in the field of view of the surgical microscope 130, which allows a surgeon to view the cross-sectional OCT image as well as the enface, fundus image with the surgical microscope 130. The cross-sectional OCT image can show anatomical features within tissue of the eye that may not be visible in the enface, fundus image. As described herein, the location indicator can be provided in the field of view of the surgical microscope 130 to assist the observer 110 in correlating, with high efficiency and high accuracy, locations within the surgical field 122 with the locations of the OCT beam and/or the OCT images.

The OCT system 182 can include various components, including an OCT beam source, a collimator, a scanner, and optics including lenses, mirrors, filters, and gratings associated with a reference arm and a sample arm. The OCT beam source can output an OCT beam directed by the scanner to scan anatomy within the surgical field 122. The scanner can include one or more of a scanning mirror, a micro-mirror device, a MEMS based device, a deformable platform, a galvanometer-based scanner, a polygon scanner, and/or a resonant PZT scanner. The scanner can direct the OCT beam in any suitable scan pattern, as described in greater detail with respect to FIGS. 9A and 9B. The OCT system 182 can be configured to split the OCT beam received from the beam source into an imaging beam directed onto target biological tissue in the surgical field 122 and a reference beam that can be directed onto a reference mirror. The OCT beam can have an operating wavelength in the 0.2-1.8 micron range, the 0.7-1.4 micron range, and/or the 0.9-1.1 micron range. Because the OCT beam employs near-infrared light, the observer 110 cannot directly visualize of the scanning location.

The OCT system 182 can be a Fourier domain (e.g., spectral domain, swept-source, etc.) or a time domain system. In a time domain system, the reference arm can be moved to different distances from the OCT beam source, allowing imaging of the target biological tissue at different depths. In a frequency domain system, spatially-encoded frequency domain (SEFD) system, spectral domain system, and/or Fourier domain system, the depth scan of the target biological tissue can be obtained by analyzing an interference signal based on the wavelength of light. Because these systems do not involve movement of physical components (e.g., the reference arm), the scanning speed can be relatively faster than the scanning speed in a time domain system. The SEFD system can utilize a dispersive detector to break up the OCT beam into beams of different wavelengths. The OCT beam source in the swept-source (SS-OCT) system can utilize a laser that rapidly sweeps across different wavelengths. The SS-OCT system can allow for simpler setup, higher resolution, and improved signal-to-noise ratio, compared to the SEFD-OCT system.

The OCT system 182 can be further configured to receive imaging light reflected from the target biological tissue in the surgical field 122. The interference pattern between the reflected imaging light and the reference beam can be utilized to generate two-dimensional or three-dimensional images of the target biological tissue. The OCT system 182 and/or the computing device 160 can generate the OCT image based on scanning the surgical field 122 using the OCT system 182. The OCT image can be made up of individual A-line scans that image a z-depth at a single point in an x-y plane of the surgical field 122. Multiple, adjacent A-line scans can be combined to form a B-scan. The B-scan can be characterized as the two-dimensional OCT image. Exemplary two-dimensional OCT images can be illustrated in FIGS. 3-8.

The OCT system 182 can include a detector configured to detect the interference pattern. The detector can include a balanced photo-detector, an InGaAs PIN detector, an InGaAs detector array, a Si PIN detector, charge-coupled devices (CCD) sensor, complementary metal-oxide-semiconductor (CMOS) sensor, pixels, or an array of any other type of sensor(s) that generate an electric signal based on detected light. Further, the detector can include a two-dimensional sensor array and a detector camera. In that regard, the imaging device 152 can include the detector, the sensor array, and/or the detector camera. For example, the imaging device 152 can be a component of the OCT system 182 and/or the ophthalmic visualization system 100. The imaging device 152 can also be a camera or video camera configured to acquire a series of still images or frames of the surgical field 122 that together form a live, real time view thereof. The imaging device 152 can be configured to receive infrared, near-infrared, visible, ultraviolet, and/or other wavelengths of light reflected from the surgical field 122. The imaging device 152 can also include processing components, memory components, and/or other electrical components to interpret the light received at the image sensor and generate image data for use by the computing device 160 communicatively coupled thereto. For example, the imaging device 150 can obtain image data representative of the real-time location of the OCT beam within the surgical field 112. The imaging device 152 can transmit the image data to the computing device 160.

The computing device 160 can be a component of the OCT system 182 and/or the ophthalmic visualization system 110. The computing device 160 can include any suitable processing circuit or computer, such as a processor communicatively coupled to a memory. The processor can execute computer instructions, such as those stored on the memory, to perform the functions described herein. The processor can be a targeted device controller and/or a microprocessor. The memory, such as semiconductor memory, RAM, FRAM, or flash memory, can interface with the processor. As such, the processor can write to and read from the memory, and perform other common functions associated with managing memory. The processing circuit of the computing device 160 can be an integrated circuit with power, input, and output pins capable of performing logic functions.

The computing device 160 can process the data acquired by the OCT system 182 to generate a two-dimensional or three-dimensional OCT image. The computing device 160 and/or the OCT system 182 can determine locations within the surgical field 122 corresponding to locations within the OCT image generated based on the scanning the surgical field 122 using the OCT system 182. The computing device 160 can also process image data acquired by the imaging device 152, such as to track the real-time location of the OCT beam within the surgical field 122. The memory of the computing device 160 can store the pre-processed and/or post-processed OCT data and/or image data. The computing device 160 can control operation of various components of the ophthalmic visualization system 100, including the on/off status, the active/inactive status, and/or the operating parameters. For example, the computing device 160 can output control signals to the OCT system 182 to initiate and to terminate scanning, to set or to change the scan pattern, etc. The computing device 160 can output control signals to the imaging device 152 to obtain image data to track the OCT beam within the surgical field 122.

The computing device 160 can generate display data representative of a graphical overlay. The computing device 160 can transmit the display data representative of the graphical overlay to the display device 172 communicatively coupled to the computing device 160. The computing device 160 can also adjust the display data, such as by modifying contrast, color tone, brightness, and/or other image parameters associated with the graphical overlay. The display device 172 can be any suitable display device configured to provide a graphical overlay into the optical path of the surgical microscope 130. The display device 172 can be projection device, such as a digital light processing (DLP) device, a liquid crystal display (LCD) device, a light emitting diode (LED) device, a liquid crystal on silicon (LCoS) device, other suitable devices, and/or combinations thereof. The display device 172 can be in optical communication with the surgical microscope 130 such that the observer 110 can view the graphical overlay while simultaneously observing the surgical field 122 using the surgical microscope 130.

Figure 3:
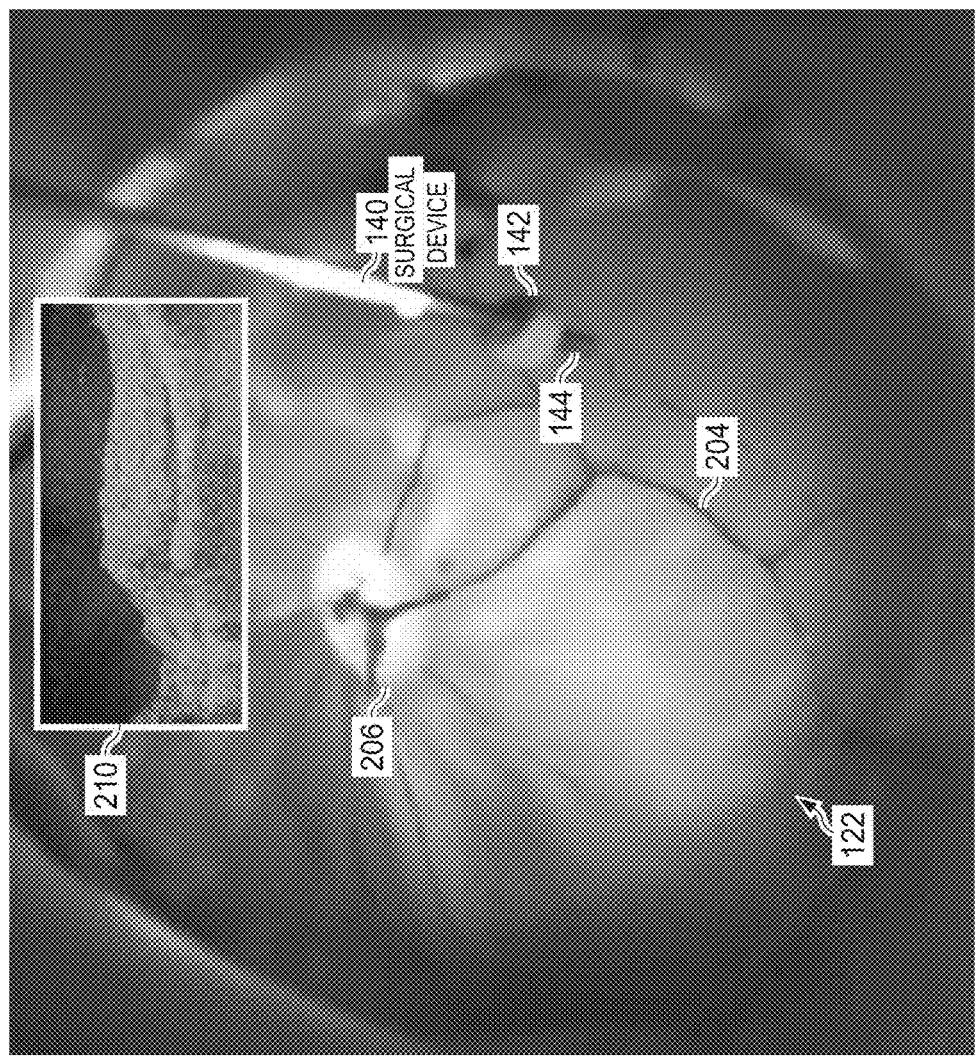
FIG. 3 is an image of a view of a surgical field using an ophthalmic visualization system.
Figure 4:
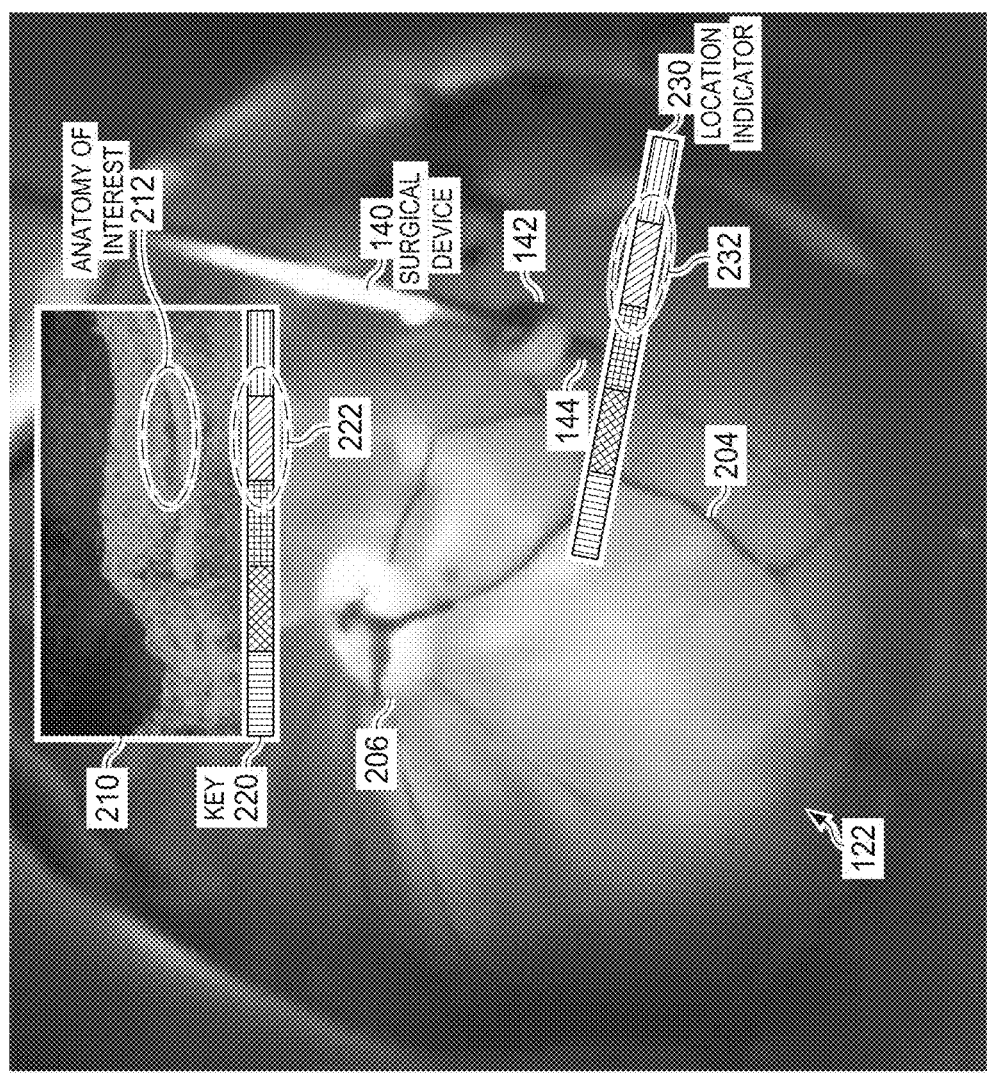
FIG. 4 is an image of a view of a surgical field using an ophthalmic visualization system.
Figure 5:
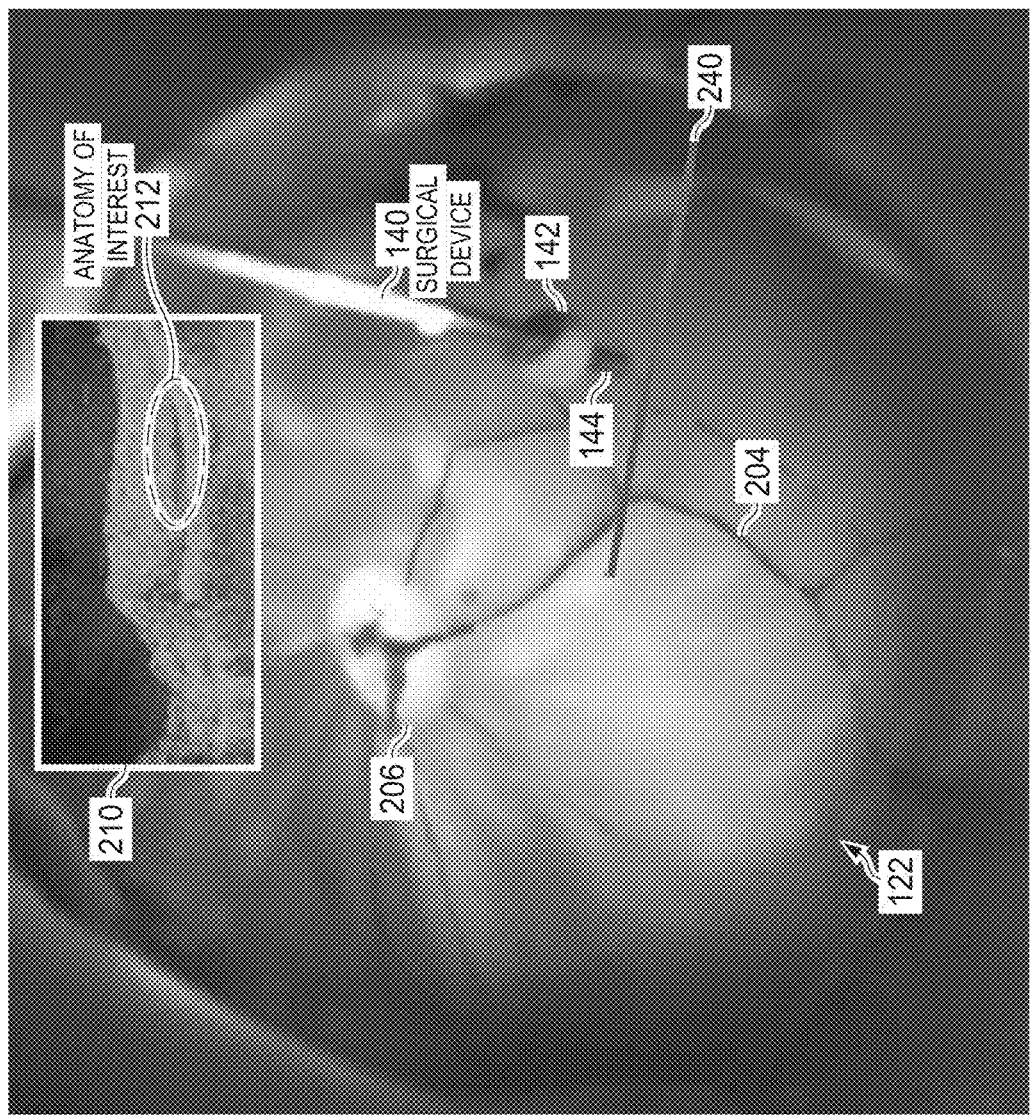
FIG. 5 is an image of a view of a surgical field using an ophthalmic visualization system.

Exemplary graphical overlays can be illustrated in FIGS. 3-9. For example, the graphical overlays can include an OCT image 210. The OCT image 210 can be overlaid onto the field of view of the surgical microscope 130. FIG. 3 shows the surgical field 122 including anatomy of the procedure eye 120, including optic disk 206 and blood vessels 204. The surgical device 140 can be positioned within the surgical field 122. The surgical device 140 can includes a tracker 142 and a tip 142. The computing device 160 can track the position of the tracker 142 and/or the tip 144 to determine the real-time position of the surgical device 140 with the surgical field 122 using image data obtained by the imaging device 152.

As described with respect to FIGS. 4 and 6-8, the indicator mechanism can output a location indicator 230 into the field of view of the surgical microscope 130. The location indicator 230 can graphically represent the locations within the surgical field corresponding to the locations within the OCT image. The corresponding locations can be identified by the computing device 160 and/or the OCT system 182. The indicator mechanism can include the display device 172. The indicator mechanism can also include any hardware associated with the display device 172 and any software executable by a processor of the computing device 160 and/or stored in a memory of the computing device 160 to control the display device 172 to output the location indicator 230. For example, the location indicator 230 can be a digital graphic output by the display device 172 as part of the graphical overlay into the field of view of the surgical microscope 130. For example, the image characteristics and/or parameters of the location indicator 230 can be generated and/or modified by the computing device 160. When the ophthalmic visualization system 100 utilizes the digital location indicator 230, less potentially harmful irradiation can be transmitted to the procedure eye 120, compared an aiming beam 240 of FIG. 5. The graphical overlay can also include a key 220. The key 220 can be positioned adjacent to and/or aligned with the OCT image 210. The key 220 and the location indicator 230 can have similar appearances and/or image characteristics. By comparing the key 220 and the location indicator 230, the observer 110 can quickly and accurately establish correlation between locations in the OCT image 210 and the surgical field 122.

In another example, the indicator mechanism can include the beam source 192. The beam source 192 can be configured to output a beam as the location indicator 230 onto the surgical field 122. The indicator mechanism can also include any hardware associated with the beam source 192 and any software executable by a processor of the computing device 160 and/or stored in a memory of the computing device 160 to control the beam source 192 to output the location indicator 230. The indicator mechanism can include combinations of the display device 172, the beam source 192, and/or associated hardware and software. FIG. 2 illustrates the ophthalmic visualization system 100 including the beam source 192. The observer 110 can view the location indicator 230, with the surgical microscope 130, when the beam source 192 transmits the location indicator 230 onto the surgical field 122. The location indicator 230 can allow the observer 110 to establish point-to-point correspondence between the OCT image 210 and the surgical field 122 regardless of whether the display device 172 or the beam source 192 outputs the location indicator 230. The beam source 192 can include a laser source, an incandescent light bulb, a halogen light bulb, a metal halide light bulb, a xenon light bulb, a mercury vapor light bulb, a light emitting diode (LED), other suitable sources, and/or combinations thereof. The beam source 192 can include a wavelength-varying or swept light source. The beam source 192 can include a fixed-wavelength light source in communication with optics, such as lenses, mirrors, filters, and/or gratings, configured to vary the wavelength or color of the light. A spot size, a spot brightness, and/or other parameters associated with the beam source 192 can also be varied. As described herein, location information correlating the OCT image 210 and the surgical field 122 can be communicated with varying wavelengths, colors, spot sizes, spot brightnesses, and/or other parameters.

The graphical overlay, including the OCT image 210, the key 220, and/or the location indicator 230 can be positioned over a portion of the field of view of the surgical microscope 130, as shown in FIGS. 3-8. The display device 172 can be configured to provide the graphical overlay with varying parameters, such as size, shape, position, transparency, etc. With a stereo microscope, one display device 170 can be provided for each of the two optical paths (e.g., one for each eye of the observer 110) or a single display device 170 can provide an output to each optical path.

Referring again to FIGS. 1 and 2, the ophthalmic visualization system 100 can also include an input device 162. The input device 162 can be in communication with the computing device 160. The input device 162 can be configured to allow the observer 110 to control ophthalmic visualization system 100, including activating/deactivating the OCT system 182, activating/deactivating OCT beam tracking, activating/deactivating the location indicator 230, selecting parameters associated with the appearance of location indicator 230, and/or other features described herein. The input device 162 may comprise any of a variety of ON/OFF switches, buttons, toggles, wheels, digital controls, touchscreen controls, or other user interface components. The input device 162 can be integrally disposed on surgical microscope 130 and/or the surgical device 140. For example, the input device 162 can include one or more button(s) on a handheld portion of the surgical device 130 such that the location indicator 230 can be selectively and instantaneously provided during the surgical procedure when the observer 110 depresses the button. The input device 162 can be a distinct component, such as, by way of non-limiting example, a surgical footswitch, a remote control device, a touchscreen control device, and/or another computing device. The ophthalmic visualization system 100 can include multiple input devices 162. The input device 162 can generate and transmit input signals based on the received user input. The computing device 160 can receive and process the input signal. The computing device 160 can generate and transmit control signals to the imaging device 152, the display device 172, the OCT system 182, and/or the beam source 192 in response to the user input. The computing device 160 can also generate and output the location indicator 230 based on the received user input.

The imaging device 152, the computing device 160, the input device 162, the display device 172, the OCT system 182, and/or the beam source 192 can be mechanically coupled to the surgical microscope 130. For example, the imaging device 152, the computing device 160, the input device 162, the display device 172, the OCT system 182, and/or the beam source 192 can be integrated with or integrally disposed on/within the surgical microscope 130.

In another example, the imaging device 152, the computing device 160, the input device 162, the display device 172, the OCT system 182, and/or the beam source 192 can be removably coupled to the surgical microscope 130. An example of a modular approach can be illustrated in FIGS. 1 and 2. In that regard, the imaging device 152 can be part of an imaging module 150, the display device 172 can be part of a display module 170, the OCT system 182 can be part of an OCT module 180, and the beam source 192 can be part of a beam module 190. The imaging module 150, the display module 170, the OCT module 180, and/or the beam module 190 can be removably coupled to surgical microscope 130. That is, a user (e.g., the observer 110, a surgeon, another physician, a nurse, a technician, etc.) can selectively add or remove one or more of the modules to selectively provide the features described herein. Thus, the imaging device 152, the display device 172, the OCT system 182, the beam source 192, and/or other components described herein can be implemented in an existing surgical microscope by adding one or more modules. Accordingly, a hospital or other ophthalmic services provider can advantageously avoid the large capital expenditure associated with the acquisition of an entire surgical microscope that includes the imaging device 152, the display device 172, the OCT system 182, and/or the beam source 192, etc.

The surgical microscope 130, the imaging module 150, and the display module 170, the OCT module 180, the beam module 190 can include various components (e.g., wires, contacts, interfaces, the lenses 132, etc.) for facilitating electrical, optical, and/or data communication between the computing device 160, the imaging device 152, the display device 172, the input device 162, the OCT system 182, and/or the beam source 192. Different combinations of components can be included in a given module. One or more of the imaging device 152, the display device 172, the OCT system 182, the beam source 192, the input device 162, and/or the computing device(s) 160 can be disposed in the same or different modules. One or more of the imaging device 152, the display device 172, the OCT system 182, the beam source 192, the input device 162, and/or the computing device(s) 160 can be distinct from the surgical microscope 130 while one or more others of the components can be mechanically coupled to the surgical microscope 130.

The surgical microscope 130 can include one or more beam directors 137 configured to guide the OCT beam from the OCT system 182 and/or the beam from the beam source 192 to the surgical field 122, to guide reflected light from the surgical field 122 to the OCT system 182 and/or the imaging device 152, to guide light from the display device 172 to the eyepiece 136, etc. In that regard, the beam directors 137 can be configured to reflect all or a portion of incident light while allowing all or another portion to pass through. For example, the beam directors 137 can be a beam splitter or a beam coupler. The beam directors 137 can include a glass prism, a metallic-coated mirror, a dichromic mirror, dichromic mirrored prism, a notch filter, a hot mirror, and/or a cold mirror. The beam directors 137 can be positioned any suitable location along the optical path, such as within or outside the surgical microscope 130. For example, the beam directors 137 can be positioned between the eyepiece 136 and the surgical field 122, including between the eyepiece 136 and the objective lens 134, as shown, between the lens 132 and the objective lens 134, between the objective lens 134 and the surgical field 122, and/or between the lens 132 and the surgical field 122. The beam directors 137 can be positioned below the objective lens 134, such as between the objective lens 134 and the surgical field 122.

FIGS. 4 and 6-8 illustrate views of the surgical field 122 using the ophthalmic visualization system 100. In that regard, the location indicator 230 can be positioned within the field of the view of the surgical microscope 130. The observer 110 can also view the OCT image 210 and the key 220 with the surgical microscope 130. The location indicator 230 can be sized, shaped, and positioned to be aligned with the B-scan of the OCT system 182. For example, the location indicator 230 can indicate where along the x-y plane of the surgical field 122 the data associated with the OCT image 210 was obtained. The location indicator 230 and the key 220 of FIG. 4 can include one, two, three, four, five, or more patterns. The patterns can correspond to a color gradient or multiple colors. The location indicator 230 can include discrete sections of patterns or colors. The location indicator 230 can include a smooth transition between different patterns or colors, such as a gradient. The location indicator 230 can include one or more colors, including a rainbow, and/or shades, hues, tints, tones, different saturations, different brightness, and/or other suitable variations of one or more colors.

The multiple patterns or colors of the location indicator 230 and the key 220 can facilitate efficient identification of locations of individual A-line scans of the OCT system 182. For example, the location indicator 230 can allow the observer 110 to quickly and accurately determine the location of an anatomy of interest 212 within the surgical field 122. The anatomy of interest 212 can be any suitable physiology, including fluid, a blood vessel, a retinal layer, a retinal abnormality, a break, a hole, a tear, a protrusion, a growth, and/or other features of the procedure eye 120. The observer 110 can identify the anatomy of interest 212 in the OCT image 210. The observer 110 can identify the position and/or range of patterns in area 222 aligned with the anatomy of interest 212 in the key 220. The observer 110 can identify the corresponding position and/or range of patterns in area 232 in the location indicator 230 to determine the location of the anatomy of interest 212 in the surgical field 212. As described with respect to FIG. 8, the computing device 160 can also identify the anatomy of interest 212. The observer 110, such as the surgeon, can perform the ophthalmic surgical procedures based on the identified anatomy of interest 212. The location indicator 230 of FIGS. 4 and 6-8 facilitate more efficient and accurate identification of the anatomy of interest 212 within the surgical field 122, compared to a monochromatic, aiming beam 240 of FIG. 5, which only illustrates a location of the B-scan, and not individual A-line scans. The observer 110 can be required to perform slow, tedious, complex, and inaccurate spatial interpretation work in his or her mind in real time during surgery in an attempt to identify corresponding locations in the OCT and fundus images with the aiming beam 240. The location indicator 230 of FIGS. 4 and 6-8 thus allows the observer 110 and/or the computing device 160 to determine, quickly and accurately, point-to-point location correspondence between the OCT image 210 and the surgical field 122.

The location indicator 230 and/or the key 220 can be based on all or a portion of the B-scan of the OCT system 182. For example, the location indicator 230 and/or the key 220 illustrated in FIGS. 4 and 6-8 can be based on a line scan of the OCT system 182. In some examples, the location indicator 230 can include a spot or a point that traces the location of the OCT beam in real-time during scanning. The B-scan and/or the OCT image 210 can also be rendered in real-time within the field of view of the surgical microscope 130. The key 220 can be similarly aligned in real-time with the current A-line scan. The location of the individual A-line scan can be communicated by the varying appearance of the spot or the point of the location indicator 230 and the key 220 as it follows or traces the location of the OCT beam. For example, wavelength, color, spot size, spot brightness, and/or other parameters can change along the B-scan. When the OCT beam scans cross different locations, the color, spot size, spot brightness, and/or other parameters of the location indicator 230 can be synchronized to change accordingly. The observer 110 and/or the computing device 160 can identify individual A-line scans by correlating the location of the spot and/or the varying wavelengths, colors, spot sizes, spot brightnesses, and/or other parameters. The location indicator 230 and/or the key 220 can include the spot indicating the current A-line scan and a trail following the spot to indicate earlier A-line scans.

Figure 6:
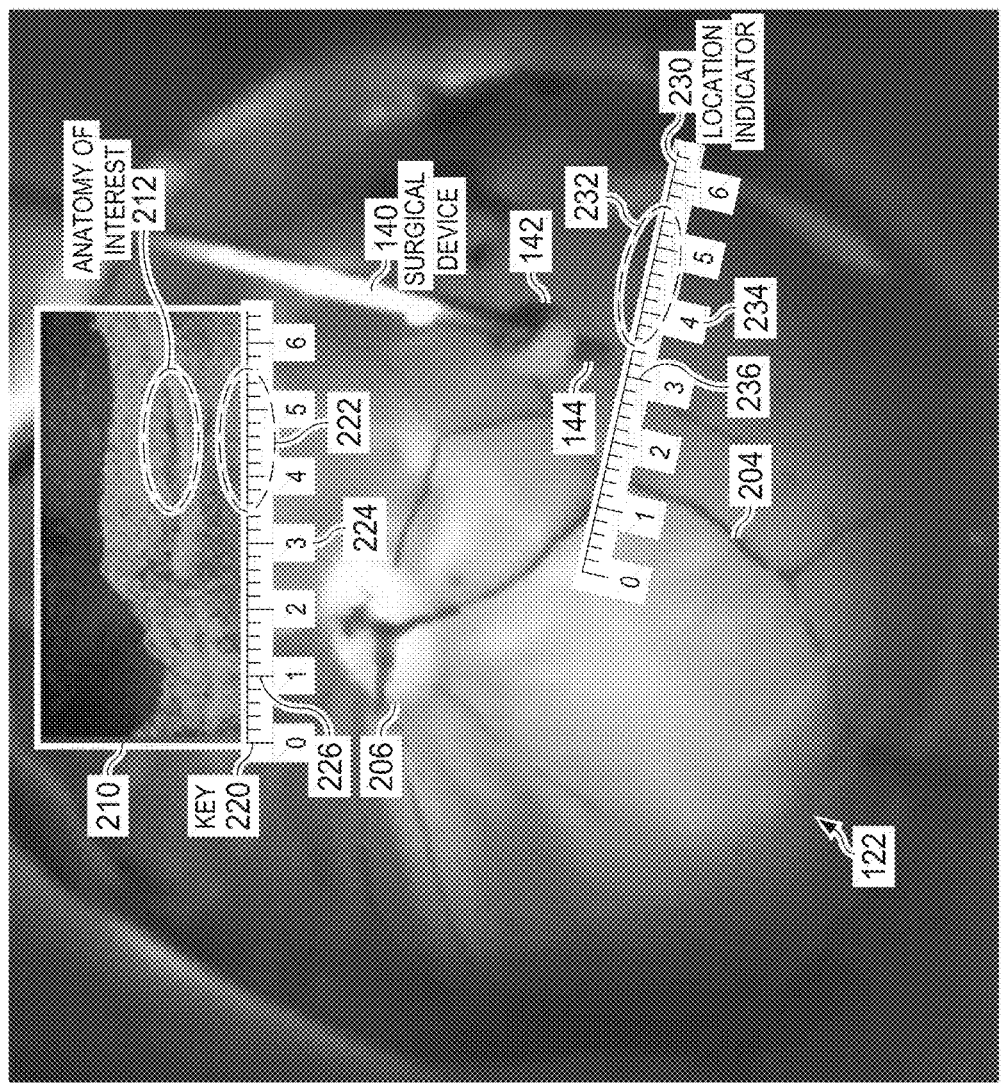
FIG. 6 is an image of a view of a surgical field using an ophthalmic visualization system.

FIG. 6 illustrates the location indicator 230 and the key 220 including a ruler to graphically represent locations within the surgical field 122 corresponding to the locations within the OCT image 182. For example, the location indicator 230 can include scale bars 236 and corresponding numerals 234. Similarly, the key 220 can include the scale bars 226 and the corresponding numerals 224. The scale bars 236 can be variously sized and shaped. For example, the location indicator 230 can include longer major scale bars and shorter minor scale bars. Any suitable length scale, such as centimeters, millimeters, microns, and/or other suitable length scales, both larger and smaller, can be used. The observer 110 and/or the computing device 160 can locate the anatomy of interest 212 from the OCT image 210 in the surgical field 122 by locating the corresponding areas 222, 232 on the key 220 and the location indicator 230, respectively. With the location indicator 230 and the key 220 including a ruler, a location coordinate associated with the anatomy of interest 212 can be determined. Using the location coordinate, the exact position of the anatomy of interest 212 in surgical field can be identified based on the corresponding location coordinate in the location indicator 230. For example, the scale bars 226 and/or the numerals 224 of the key 220 can be used to establish point-to-point correspondence with the scale bars 236 and/or the numerals 234 of the location indicator 230.

Figure 7:
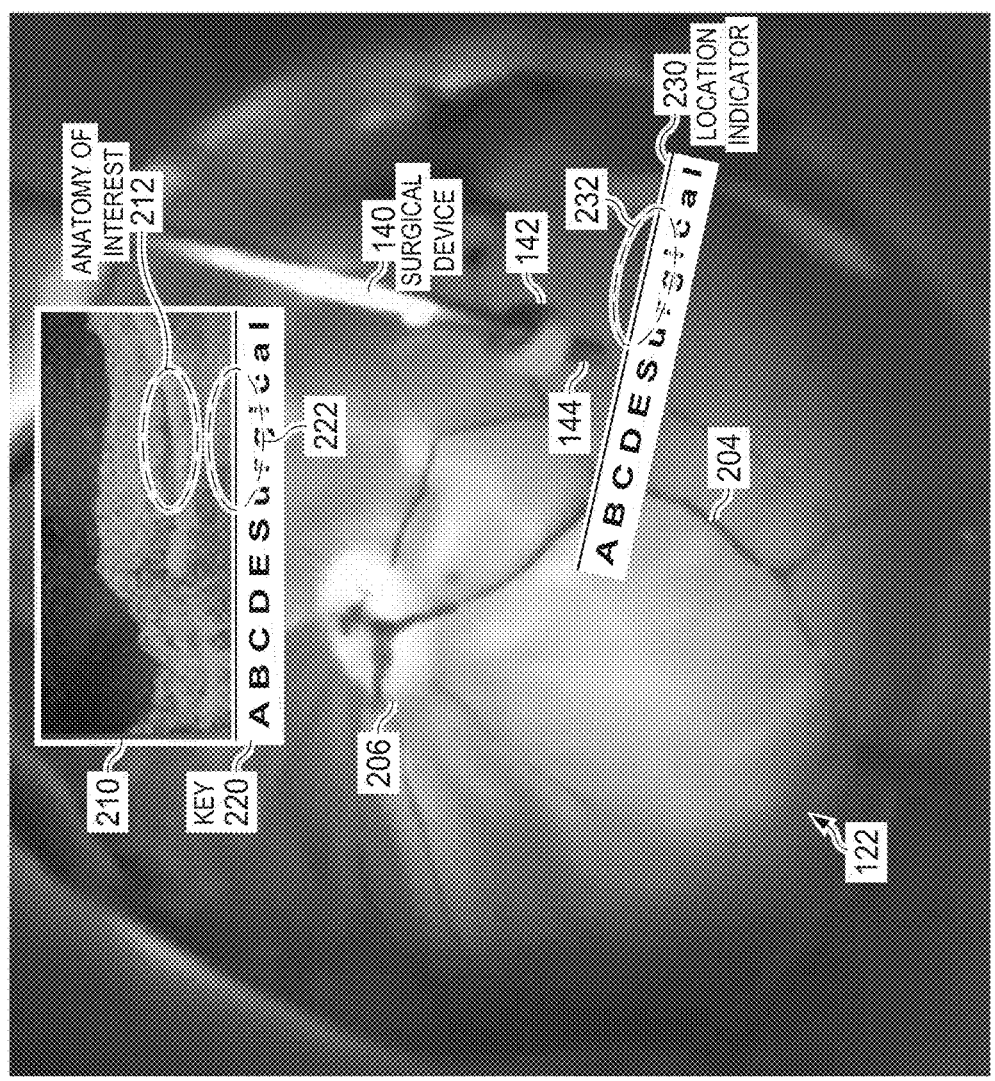
FIG. 7 is an image of a view of a surgical field using an ophthalmic visualization system.

FIG. 7 illustrates the location indicator 230 and the key 220 including text to graphically represent locations within the surgical field 122 corresponding to the locations within the OCT image 182. For example, the location indicator 230 and/or the key 220 can include capital and/or lowercase letters. For example, the key 220 of FIG. 7 includes the text "ABCDESurgical." Any text can be utilized for the key 220, including a random string of letters, letters forming recognizable word(s), such as the name of a manufacturer of the ophthalmic visualization system 100 and/or a component thereof, and/or other suitable text. The observer 110 and/or the computing device 160 can locate the anatomy of interest 212 from the OCT image 210 in the surgical field 122 by locating the corresponding areas 222, 232 on the key 220 and the location indicator 230, respectively. For example, the letters of the key 220 can be used as location coordinates to establish point-to-point correspondence with the letters of the location indicator 230.

Figure 8:
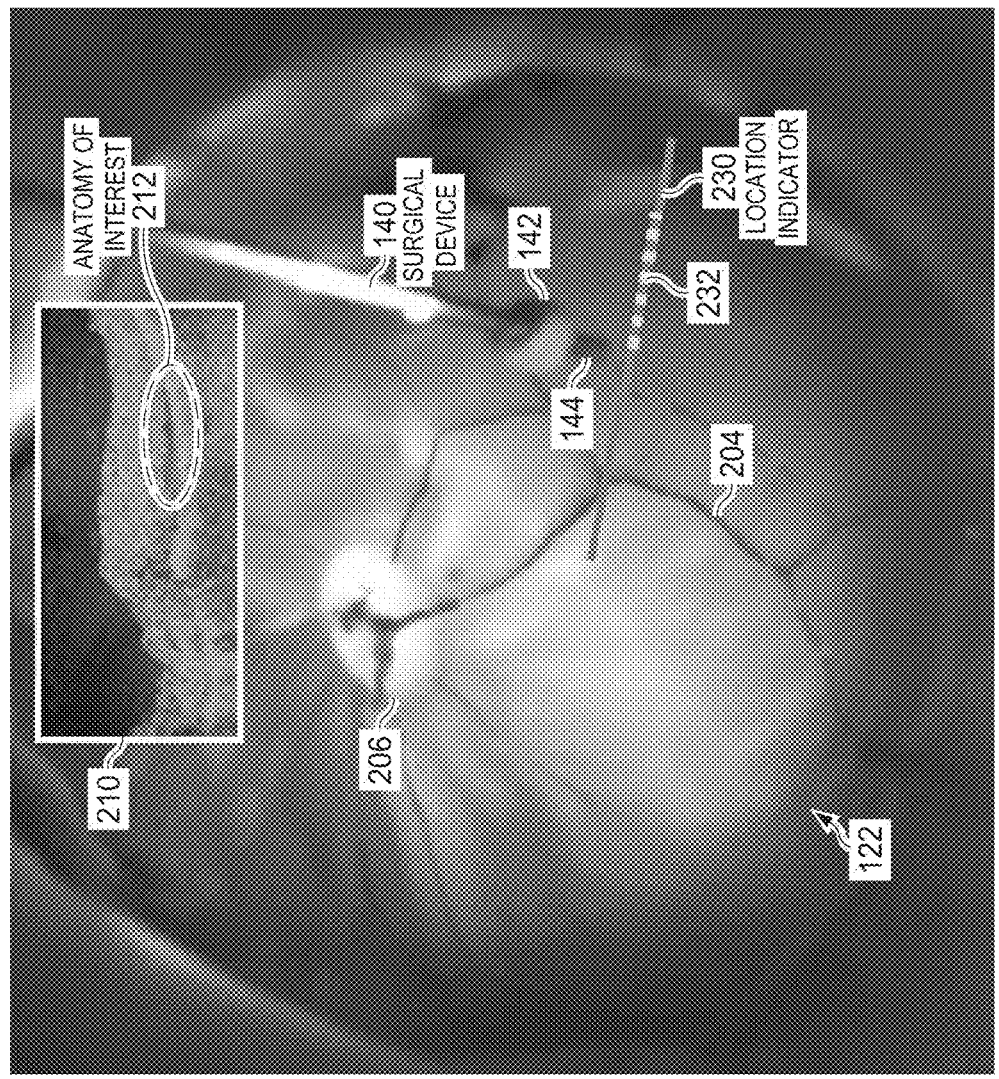
FIG. 8 is an image of a view of a surgical field using an ophthalmic visualization system.

FIG. 8 illustrates the location indicator 230 including a marker 232 graphically representing the anatomy of interest 212 in the surgical field 212. For example, the computing device 160 can process the OCT data obtained by the OCT system 182 and the image data acquired by the imaging device 152 to identify the anatomy of interest 212 within the OCT image 210 and its corresponding location in the surgical field 122. The marker 232 can be automatically positioned within the field of view of the surgical microscope 130 to guide the surgical intervention. The marker 232 illustrated in FIG. 8 includes spaced squares to identify the area in the surgical field 122 corresponding to the anatomy of interest 212. The marker 232 can include any suitable text, numerals, shapes, symbols, colors, patterns, images, scale bars, a color gradient, a ruler, and/or beam spots of varying wavelength, varying spot size, and/or varying brightness that graphically represent the anatomy of interest 212.

While FIGS. 4 and 6-8 illustrate particular examples, the location indicator 230 and the key 220 can be variously sized, shaped, and/or positioned to graphically represent locations within the surgical field 122 corresponding to the locations within the OCT image 182. For example, the location indicator 230 and the key 220 can include any suitable text, numerals, shapes, symbols, colors, patterns, images, scale bars, a color gradient, a ruler, and/or beam spots of varying wavelength, varying spot size, and/or varying brightness. The appearance and/or image characteristics can be selected by observer 110, such as with a user input at the input device 162.

FIGS. 9A, 9B, 9C, and 9D illustrate a scan pattern 300 of the OCT system 182 and different location indicators associated therewith. The scanner of the OCT system 182 can scan the OCT beam over any desired one-dimensional or two-dimensional scan patterns, including a line, a spiral, a raster, a circle, a cross, a constant-radius asterisk, a multiple-radius asterisk, a multiply folded path, and/or other scan patterns. Line scans or portions of raster, cross, and/or asterisk scans can be illustrated in FIGS. 4-8.

Figure 9A:
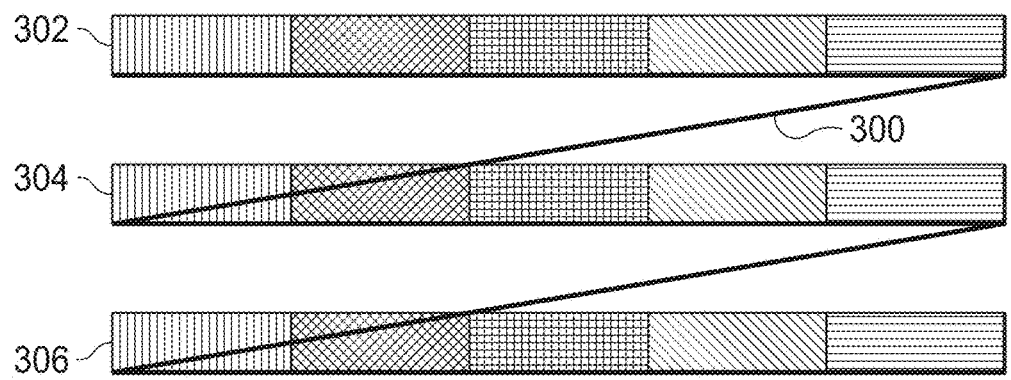
FIG. 9A is a scan pattern of an OCT system and associated location indicators.
Figure 9B:
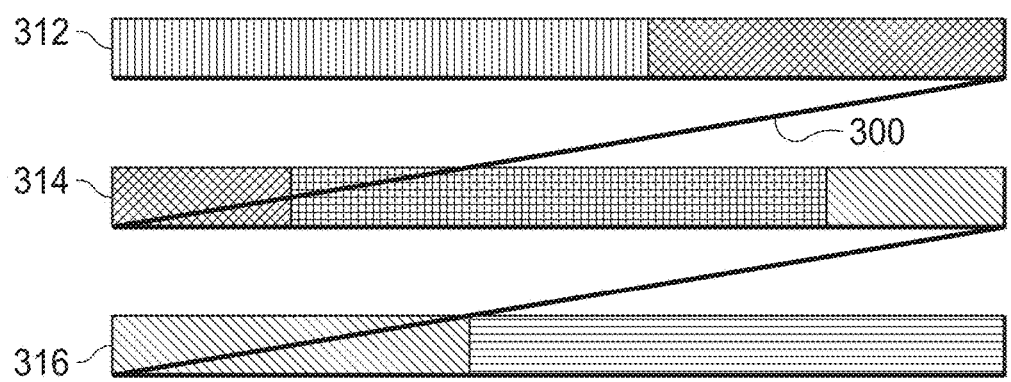
FIG. 9B is a scan pattern of an OCT system and associated location indicators.
Figure 9C:
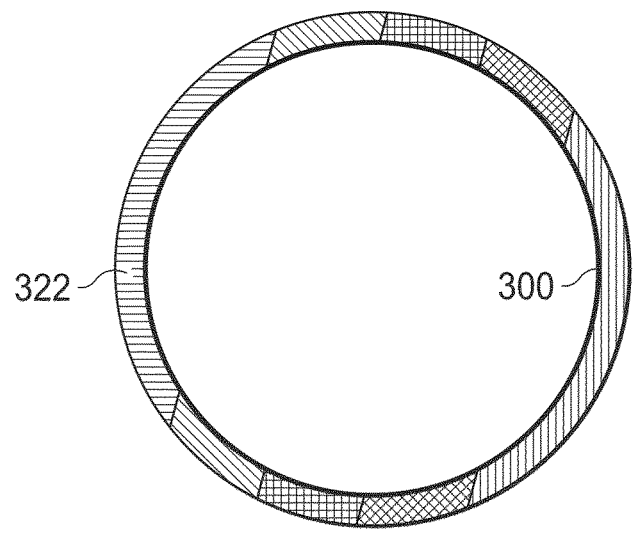
FIG. 9C is a scan pattern of an OCT system and an associated location indicator.
Figure 9D:
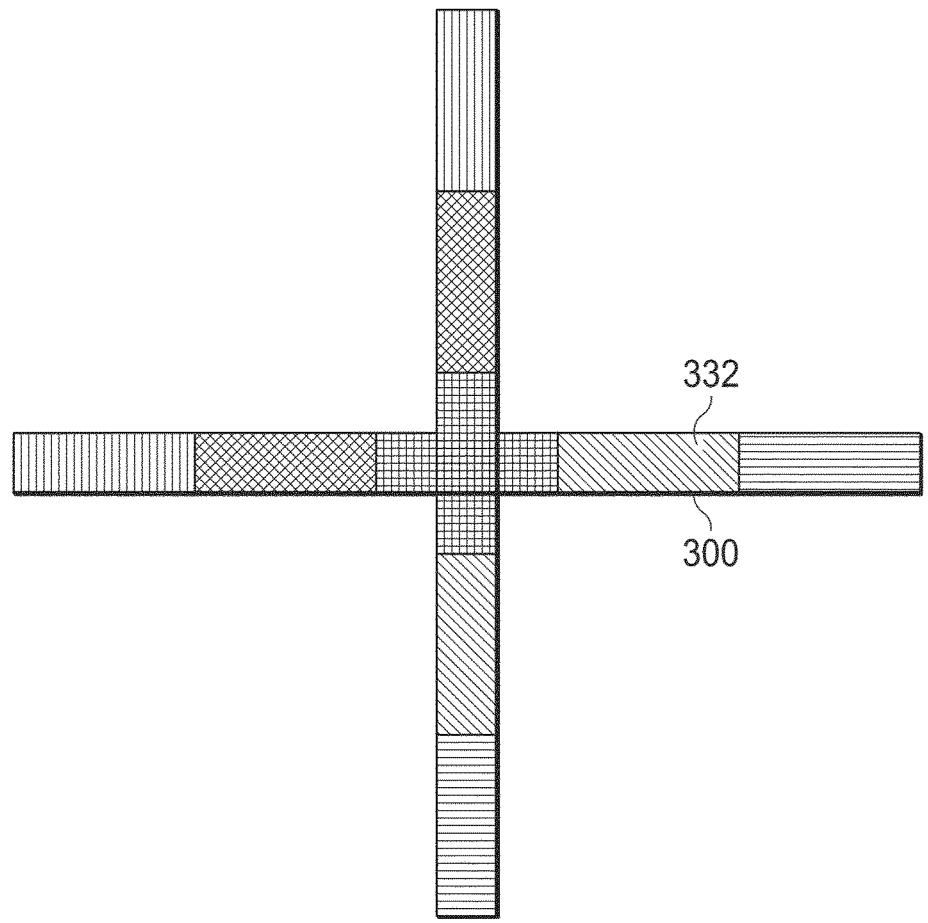
FIG. 9D is a scan pattern of an OCT system and associated location indicators.

Scan pattern 300 of FIGS. 9A and 9B can be raster scans or portions thereof. Scan pattern 300 of FIG. 9C can be circular scan. Scan pattern 300 of FIG. 9D can be a cross scan or a portion of an asterisk scan. One or more of location indicators 302, 304, 306 (FIG. 9A), one or more location indicators 312, 314, 316 (FIG. 9B), location indicator 322 (FIG. 9C), and/or location indicator 332 (FIG. 9D) can be positioned within the field of view of the surgical microscope 130, along with the corresponding OCT images. Image characteristics, such as the size, shape, position, and/or other visual features, of the location indicators 302, 304, 306, 312, 314, 316 can be based on the scan pattern 300 of the OCT system 182. The key 220 corresponding to the location indicators can have similar image characteristics.

Individual A-line scans of the OCT system 182 can be identified with respect to a portion of entire scan pattern 300, as illustrated by the location indicators 302, 304, 306 (FIG. 9A). In that regard, each of the location indicators 302, 304, 306 has a similar appearance or image characteristics (e.g., the same pattern or color gradient in FIG. 9A, though any suitable image characteristics can be used) such that each horizontal portion of the raster scan can be individually considered. For example, each of the location indicators 302, 304, 306 can be a gradient including the same five patterns.

Individual A-line scans of the OCT system 182 can also be identified with respect to the entire scan pattern 300, as illustrated by the location indicators 312, 314, 316 (FIG. 9B). In that regard, the location indicators 312, 314, 316 each have different appearances or image characteristics (e.g., different pattern or color gradients in FIG. 9B, though any suitable image characteristics can be used) such that each horizontal portion of the raster scan can be considered as part of the whole raster scan. For example, the location indicators 312, 314, 316 collectively can be a pattern or color gradient including five patterns or colors, with each of the location indicators 312, 314, 316 including two or three of the patterns or colors.

Embodiments as described herein can provide devices, systems, and methods including location indicators having varying appearances and/or image characteristics that illustrate point-to-point correspondence. The location indicators can facilitate efficient and accurate identification of corresponding locations in OCT images and the surgical field. The examples provided above can be exemplary in nature and not limiting. One skilled in the art may readily devise other systems consistent with the disclosed embodiments intended to be within the scope of this disclosure. As such, the application can be limited only by the following claims.

The invention claimed is:

1. An ophthalmic visualization system, comprising:
a computing device in communication with an optical coherence tomography ("OCT") system configured to scan a surgical field to generate an OCT image, the computing device configured to determine locations within a microscope image of the surgical field provided by a surgical microscope corresponding to locations within the OCT image; and
an indicator mechanism communicatively coupled with the computing device and the surgical microscope configured to provide the microscope image of the surgical field,
wherein the indicator mechanism is configured to cause a location indicator to be positioned within the microscope image provided by the surgical microscope, and wherein the location indicator indicates where, along an x-y plane of the microscope image, data associated with the OCT image was obtained, and graphically represents the locations within the microscope image of the surgical field provided by the surgical microscope corresponding to the locations within the OCT image;
wherein the computing device comprises a processor configured to execute instructions stored in a memory.

2. The system of claim 1, wherein the indicator mechanism comprises:
a display device configured to output a graphical overlay including the location indicator into a field of view of the surgical microscope.

3. The system of claim 2, wherein:
the location indicator includes at least one of text, numerals, shapes, symbols, colors, patterns, images, scale bars, a color gradient, or a ruler.

4. The system of claim 2, wherein the graphical overlay further includes:
the OCT image; and
a key, positioned adjacent to the OCT image and corresponding to the location indicator.

5. The system of claim 2, wherein:
the computing device is configured to identify an anatomy of interest within the OCT image; and
the location indicator graphically represents the anatomy of interest.

6. The system of claim 5, wherein:
the location indicator is configured to graphically represent the anatomy of interest using at least one of text, numerals, shapes, symbols, colors, patterns, images, scale bars, a color gradient, or a ruler.

7. The system of claim 1, wherein:
image characteristics of the location indicator are based on a scan pattern of the OCT system.

8. The system of claim 7, wherein:
the OCT system comprises a spectral domain or a Fourier domain system.

9. The system of claim 7, wherein:
the OCT system comprises a swept source system.

10. The system of claim 1, wherein the indicator mechanism includes:
a beam source, configured to output a beam as the location indicator onto the surgical field.

11. The system of claim 10, wherein:
at least one of wavelengths, spot sizes, or spot brightnesses of the beam graphically represent the locations within the surgical field corresponding to the location within the OCT image.

12. The system of claim 10, wherein the beam source includes:
a swept light source.

13. The system of claim 10, wherein the beam source includes:
a light source in communication with a filter configured to vary at least one of the wavelengths, the spot sizes, or the spot brightness of the beam.

14. The system of claim 10, further comprising:
a display device in communication with the surgical microscope and configured to output the OCT image and a key corresponding to the location indicator adjacent to the OCT image in a field of view of the surgical microscope.

15. A method of visualizing an ophthalmic surgical procedure, the method comprising:
scanning a surgical field using an OCT imaging system;
obtaining a microscope image of the surgical field using a surgical microscope;
determining, using a computing device in communication with the OCT imaging system and the surgical microscope, locations within the microscope image of the surgical field corresponding to locations within an OCT image generated based on the scanning the surgical field using the OCT imaging system; and
outputting a location indicator within a field of view of the surgical microscope viewing the microscope image of the surgical field, wherein the location indicator indicates where, along an x-y plane of the microscope, image data associated with the OCT image was obtained and graphically represents the locations within the microscope image of the surgical field corresponding to the locations within the OCT image.

16. The method of claim 15, wherein the outputting the location indicator comprises:
outputting, using a display device in communication with the surgical microscope, a graphical overlay including the location indicator into the field of view of the surgical microscope.

17. The method of claim 15, wherein the outputting the location indicator comprises:
outputting, using a beam source in communication with the surgical microscope, the location indicator onto the surgical field.

18. An ophthalmic visualization system, comprising:
a surgical microscope configured to provide a microscope image of a surgical field;
an optical coherence tomography ("OCT") system configured to scan a portion of the surgical field to generate an OCT image;
a processor communicatively coupled with the OCT system and the surgical microscope, the processor configured to execute instructions stored in a memory to determine locations in the microscope image which correspond to locations within the OCT image; and
an indicator mechanism comprising at least one of a display and a beam source, the indicator mechanism communicatively coupled with the processor and the surgical microscope and configured to cause a location indicator to be positioned within the microscope image of the surgical field, the location indicator indicating where along an x-y plane of the microscope image of the surgical field data associated with the OCT image was obtained, wherein the location indicator comprises varying image characteristics across a length of the location indicator to graphically represent the locations in the microscope image which correspond to the locations within the OCT image.

* * * * *